(12) United States Patent
Subramani et al.

(10) Patent No.: US 10,121,655 B2
(45) Date of Patent: Nov. 6, 2018

(54) LATERAL PLASMA/RADICAL SOURCE

(71) Applicant: Applied Materials, Inc., Santa Clara, CA (US)

(72) Inventors: Anantha K. Subramani, San Jose, CA (US); Kaushal Gangakhedkar, San Jose, CA (US); Abhishek Chowdhury, Bangalore (IN); John C. Forster, Mt. View, CA (US); Nattaworn Nuntaworanuch, Milpitas, CA (US); Kallol Bera, Fremont, CA (US); Philip A. Kraus, San Jose, CA (US); Farzad Houshmand, Santa Clara, CA (US)

(73) Assignee: APPLIED MATERIALS, INC., Santa Clara, CA (US)

( * ) Notice: Subject to any disclaimer, the term of this patent is extended or adjusted under 35 U.S.C. 154(b) by 0 days.

(21) Appl. No.: 15/353,315

(22) Filed: Nov. 16, 2016

(65) Prior Publication Data

US 2017/0148626 A1    May 25, 2017

Related U.S. Application Data

(60) Provisional application No. 62/258,386, filed on Nov. 20, 2015.

(51) Int. Cl.
*H01L 21/687* (2006.01)
*H01L 21/02* (2006.01)
(Continued)

(52) U.S. Cl.
CPC .... *H01L 21/0234* (2013.01); *C23C 16/45536* (2013.01); *C23C 16/45551* (2013.01);
(Continued)

(58) Field of Classification Search
CPC ......... C23C 16/45536; C23C 16/45551; H01J 37/32082; H01J 37/3244; H01J 37/32449;
(Continued)

(56) References Cited

U.S. PATENT DOCUMENTS 5,866,871 A * 2/1999 Birx .................. H01J 27/04
219/121.48
5,981,399 A 11/1999 Kawamura et al.
(Continued)

FOREIGN PATENT DOCUMENTS

JP   2003338399 A   11/2003
JP   2008172168 A    7/2008
(Continued)

OTHER PUBLICATIONS

Yokoyama, Shin et al., "Atomic-layer selective deposition of silicon nitride on hydrogen-terminated Si surfaces", Applied Surface Science 130-132 (1998), pp. 352-356.

*Primary Examiner* — Mary Wilczewski
(74) *Attorney, Agent, or Firm* — Servilla Whitney LLC

(57) ABSTRACT

Plasma source assemblies comprising a housing with an RF hot electrode and a return electrode are described. The housing includes a gas inlet and a front face defining a flow path. The RF hot electrode includes a first surface oriented substantially parallel to the flow path. The return electrode includes a first surface oriented substantially parallel to the flow path and spaced from the first surface of the RF hot electrode to form a gap. Processing chambers incorporating the plasma source assemblies and methods of using the plasma source assemblies are also described.

14 Claims, 9 Drawing Sheets

(51) Int. Cl.
*H01L 21/285* (2006.01)
*C23C 16/455* (2006.01)
*H01J 37/32* (2006.01)

(52) U.S. Cl.
CPC .... *H01J 37/3244* (2013.01); *H01J 37/32082* (2013.01); *H01J 37/32449* (2013.01); *H01J 37/32541* (2013.01); *H01J 37/32568* (2013.01); *H01L 21/0228* (2013.01); *H01L 21/28556* (2013.01); *H01L 21/68764* (2013.01); *H01L 21/68771* (2013.01); *H01L 21/68785* (2013.01)

(58) Field of Classification Search
CPC ........... H01J 37/32541; H01J 37/32568; H01J 27/04; H01L 21/0228; H01L 21/0234; H01L 21/28556; H01L 21/68764; H01L 21/68771; H01L 21/68785; F03H 1/0087
See application file for complete search history.

(56) References Cited

U.S. PATENT DOCUMENTS

| | | |
|---|---|---|
| 6,071,055 A | 6/2000 | Tepman |
| 6,084,198 A * | 7/2000 | Birx ..................... H01J 27/04 219/121.48 |
| 6,106,634 A | 8/2000 | Ghanayem et al. |
| 6,172,324 B1 * | 1/2001 | Birx ..................... H05G 2/003 219/121.48 |
| 6,192,601 B1 | 2/2001 | Ghanayem et al. |
| 6,300,720 B1 * | 10/2001 | Birx ..................... F03H 1/0087 315/111.21 |
| 6,315,512 B1 | 11/2001 | Tabrizi et al. |
| 6,395,094 B1 | 5/2002 | Tanaka et al. |
| 6,616,986 B2 | 9/2003 | Sherman |
| 6,630,413 B2 | 10/2003 | Todd |
| 6,652,924 B2 | 11/2003 | Sherman |
| 6,818,517 B1 | 11/2004 | Maes |
| 6,821,825 B2 | 11/2004 | Todd et al. |
| 6,824,816 B2 | 11/2004 | Aaltonen et al. |
| 6,878,628 B2 | 4/2005 | Sophie et al. |
| 6,936,535 B2 | 8/2005 | Kim et al. |
| 7,006,888 B2 | 2/2006 | Wang et al. |
| 7,056,835 B2 | 6/2006 | Pomarede et al. |
| 7,092,287 B2 | 8/2006 | Beulens et al. |
| 7,108,747 B1 | 9/2006 | Leskelä et al. |
| 7,172,792 B2 | 2/2007 | Wang et al. |
| 7,202,166 B2 | 4/2007 | Wilk |
| 7,241,677 B2 | 7/2007 | Soininen et al. |
| 7,294,582 B2 | 11/2007 | Haverkort et al. |
| 7,297,641 B2 | 11/2007 | Todd et al. |
| 7,323,422 B2 | 1/2008 | Raaijmakers et al. |
| 7,329,590 B2 | 2/2008 | Elers et al. |
| 7,462,571 B2 | 12/2008 | Hasebe et al. |
| 7,479,454 B2 | 1/2009 | O'Meara et al. |
| 7,494,937 B2 | 2/2009 | Clark |
| 7,531,452 B2 | 5/2009 | Clark |
| 7,585,752 B2 | 9/2009 | Todd et al. |
| 7,604,841 B2 | 10/2009 | Joe et al. |
| 7,625,609 B2 | 12/2009 | Matsuura |
| 7,629,224 B1 | 12/2009 | Van Den Hoek et al. |
| 7,629,270 B2 | 12/2009 | Swerts et al. |
| 7,651,953 B2 | 1/2010 | Todd et al. |
| 7,651,961 B2 | 1/2010 | Clark |
| 7,695,233 B2 | 4/2010 | Toshima |
| 7,737,051 B2 | 6/2010 | Dip et al. |
| 7,758,920 B2 | 7/2010 | Hasebe et al. |
| 7,785,658 B2 | 8/2010 | Shinriki et al. |
| 7,807,586 B2 | 10/2010 | Clark |
| 7,897,217 B2 | 3/2011 | Faguet |
| 7,919,416 B2 | 4/2011 | Lee et al. |
| 7,939,455 B2 | 5/2011 | Clark |
| 7,964,513 B2 | 6/2011 | Todd et al. |
| 7,964,516 B2 | 6/2011 | Okada et al. |
| 7,972,980 B2 | 7/2011 | Lee et al. |
| 7,988,813 B2 | 8/2011 | Chen |
| 8,025,931 B2 | 9/2011 | Chou et al. |
| 8,029,226 B2 | 10/2011 | Van Der Meulen |
| 8,058,728 B2 | 11/2011 | Ishizaka et al. |
| 8,080,290 B2 | 12/2011 | Hasebe et al. |
| 8,119,540 B2 | 2/2012 | Clark |
| 8,119,544 B2 | 2/2012 | Hasebe et al. |
| 8,142,862 B2 | 3/2012 | Lee et al. |
| 8,168,548 B2 | 5/2012 | Leusink |
| 8,178,448 B2 | 5/2012 | Nodera et al. |
| 8,187,486 B1 | 5/2012 | Liu et al. |
| 8,202,803 B2 | 6/2012 | Feurprier et al. |
| 8,216,648 B2 | 7/2012 | Matsunaga et al. |
| 8,236,700 B2 | 8/2012 | Cole et al. |
| 8,242,015 B2 | 8/2012 | Matsumoto et al. |
| 8,247,030 B2 | 8/2012 | Suzuki et al. |
| 8,258,571 B2 | 9/2012 | Endoh et al. |
| 8,500,388 B2 | 8/2013 | Van Der Meulen et al. |
| 8,523,507 B2 | 9/2013 | Van Der Meulen |
| 9,117,636 B2 * | 8/2015 | Koo ............... H01J 37/32348 |
| 2003/0113188 A1 | 6/2003 | Pool |
| 2003/0133773 A1 | 7/2003 | Wang et al. |
| 2004/0091349 A1 | 5/2004 | Tabrizi et al. |
| 2005/0063800 A1 | 3/2005 | Kurita et al. |
| 2005/0068519 A1 | 3/2005 | O'Meara et al. |
| 2005/0070104 A1 | 3/2005 | O'Meara et al. |
| 2005/0199877 A1 | 9/2005 | Dip et al. |
| 2005/0211264 A1 | 9/2005 | Kostenko et al. |
| 2005/0221001 A1 | 10/2005 | Joe et al. |
| 2005/0221002 A1 | 10/2005 | Nakamura et al. |
| 2005/0269651 A1 | 12/2005 | Chen et al. |
| 2006/0022228 A1 | 2/2006 | Hoshi |
| 2006/0156979 A1 | 7/2006 | Thakur et al. |
| 2006/0213437 A1 | 9/2006 | Ishizaka et al. |
| 2006/0216418 A1 | 9/2006 | Matsuura |
| 2007/0057352 A1 | 3/2007 | Wirth et al. |
| 2007/0082130 A1 | 4/2007 | Shinriki et al. |
| 2007/0082132 A1 | 4/2007 | Shinriki et al. |
| 2007/0116887 A1 | 5/2007 | Faguet |
| 2007/0116888 A1 | 5/2007 | Faguet |
| 2007/0207014 A1 | 9/2007 | Toshima |
| 2007/0238268 A1 | 10/2007 | Leusink |
| 2007/0264106 A1 | 11/2007 | Van Der Meulen |
| 2008/0038936 A1 | 2/2008 | Todd et al. |
| 2008/0078987 A1 | 4/2008 | Leusink |
| 2008/0081470 A1 | 4/2008 | Clark |
| 2008/0093711 A1 | 4/2008 | Raaijmakers et al. |
| 2008/0131237 A1 | 6/2008 | Van Der Meulen |
| 2008/0132083 A1 | 6/2008 | Matsuura |
| 2008/0171435 A1 | 7/2008 | Fujii |
| 2008/0187417 A1 | 8/2008 | Van Der Meulen et al. |
| 2008/0187418 A1 | 8/2008 | Van Der Meulen et al. |
| 2008/0223873 A1 | 9/2008 | Chen et al. |
| 2008/0226429 A1 | 9/2008 | Van Der Meulen |
| 2008/0232933 A1 | 9/2008 | Kiley |
| 2008/0232948 A1 | 9/2008 | Van Der Meulen et al. |
| 2008/0237859 A1 | 10/2008 | Ishizaka et al. |
| 2008/0241388 A1 | 10/2008 | Clark |
| 2008/0242077 A1 | 10/2008 | Clark |
| 2008/0242116 A1 | 10/2008 | Clark |
| 2008/0274605 A1 | 11/2008 | Hoshi et al. |
| 2009/0014423 A1 * | 1/2009 | Li .................. B01J 19/088 219/121.47 |
| 2009/0035927 A1 | 2/2009 | Olsen et al. |
| 2009/0039518 A1 | 2/2009 | Feurprier |
| 2009/0079016 A1 | 3/2009 | Chen et al. |
| 2009/0087286 A1 | 4/2009 | Van Der Meulen |
| 2009/0102385 A1 | 4/2009 | Wi |
| 2009/0155606 A1 | 6/2009 | Yoon et al. |
| 2009/0191722 A1 | 7/2009 | Hasebe et al. |
| 2009/0226611 A1 | 9/2009 | Suzuki et al. |
| 2009/0233454 A1 | 9/2009 | Okada et al. |
| 2009/0246973 A1 | 10/2009 | Clark |
| 2009/0246974 A1 | 10/2009 | Clark |
| 2009/0253221 A1 | 10/2009 | Katsuki et al. |
| 2009/0311857 A1 | 12/2009 | Todd et al. |
| 2010/0006543 A1 | 1/2010 | Sawada et al. |
| 2010/0062592 A1 | 3/2010 | Clark |

(56) References Cited

U.S. PATENT DOCUMENTS

| | | |
|---|---|---|
| 2010/0078818 A1 | 4/2010 | Ishizaka et al. |
| 2010/0124618 A1 | 5/2010 | Kobayashi et al. |
| 2010/0124621 A1 | 5/2010 | Kobayashi et al. |
| 2010/0140802 A1 | 6/2010 | Matsumoto et al. |
| 2010/0144162 A1 | 6/2010 | Lee et al. |
| 2010/0162955 A1 | 7/2010 | Lei et al. |
| 2010/0173495 A1 | 7/2010 | Thakur et al. |
| 2010/0184302 A1 | 7/2010 | Lee et al. |
| 2010/0193955 A1 | 8/2010 | Milligan et al. |
| 2010/0221925 A1 | 9/2010 | Lee et al. |
| 2010/0227059 A1 | 9/2010 | Kato et al. |
| 2010/0248464 A1 | 9/2010 | Clark |
| 2010/0283097 A1 | 11/2010 | Endoh et al. |
| 2010/0304047 A1 | 12/2010 | Yang et al. |
| 2010/0304574 A1 | 12/2010 | Nodera et al. |
| 2010/0323529 A1 | 12/2010 | Honda et al. |
| 2011/0021033 A1 | 1/2011 | Ikeuchi et al. |
| 2011/0039389 A1 | 2/2011 | Yamashita et al. |
| 2011/0039416 A1 | 2/2011 | Cole et al. |
| 2011/0129618 A1 | 6/2011 | Matsunaga et al. |
| 2011/0129619 A1 | 6/2011 | Matsunaga et al. |
| 2011/0143542 A1 | 6/2011 | Feurprier et al. |
| 2011/0241128 A1 | 10/2011 | O'Meara et al. |
| 2011/0275166 A1 | 11/2011 | Shero et al. |
| 2011/0306214 A1 | 12/2011 | Zin |
| 2012/0014769 A1 | 1/2012 | Van Der Meulen et al. |
| 2012/0028469 A1 | 2/2012 | Onizawa et al. |
| 2012/0052693 A1 | 3/2012 | Ozaki et al. |
| 2012/0058282 A1 | 3/2012 | Hong et al. |
| 2012/0111831 A1 | 5/2012 | Ha |
| 2012/0164842 A1 | 6/2012 | Watanabe et al. |
| 2012/0164848 A1 | 6/2012 | Fujii et al. |
| 2012/0178264 A1 | 7/2012 | Murakami et al. |
| 2012/0196048 A1 | 8/2012 | Ueda |
| 2012/0210937 A1 | 8/2012 | Thakur et al. |
| 2012/0211873 A1 | 8/2012 | Oyama et al. |
| 2012/0214318 A1 | 8/2012 | Fukazawa et al. |
| 2012/0255678 A1 | 10/2012 | Holland et al. |
| 2013/0078823 A1 | 3/2013 | Takeshima et al. |
| 2013/0276983 A1 | 10/2013 | Park et al. |
| 2014/0271083 A1 | 9/2014 | Caveney |
| 2014/0273527 A1 | 9/2014 | Niskanen et al. |
| 2014/0290212 A1* | 10/2014 | Knauer ................. B64G 1/406 60/211 |
| 2017/0148626 A1* | 5/2017 | Subramani .......... H01L 21/0228 |
| 2017/0213701 A1* | 7/2017 | Subramani ........ H01J 37/32091 |
| 2017/0213702 A1* | 7/2017 | Hammond, IV .. H01J 37/32091 |
| 2017/0306494 A1* | 10/2017 | Lin ....................... C23C 16/509 |

FOREIGN PATENT DOCUMENTS

| | | | |
|---|---|---|---|
| JP | 2009105030 A | 5/2009 | |
| JP | 2013084898 A | 5/2013 | |
| JP | 2014509066 A | 4/2014 | |
| JP | 2017-135359 * | 8/2017 | ............ H01L 21/31 |
| KR | 1020120115539 A | 10/2012 | |
| WO | 99/18603 A1 | 4/1999 | |
| WO | 99/28951 A3 | 6/1999 | |
| WO | 00/30155 A1 | 5/2000 | |

* cited by examiner

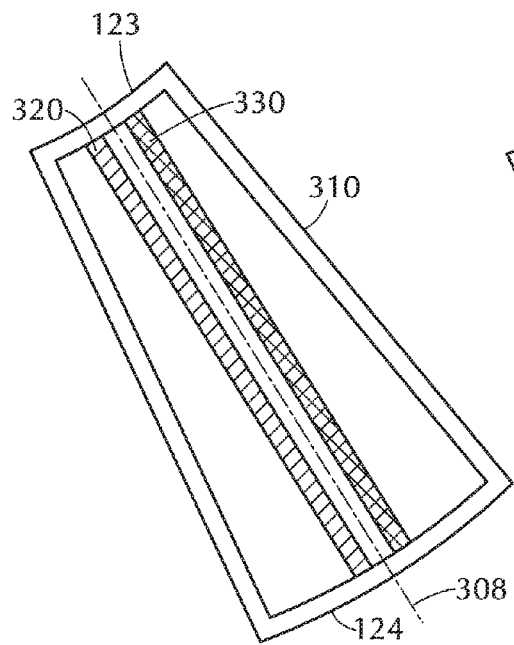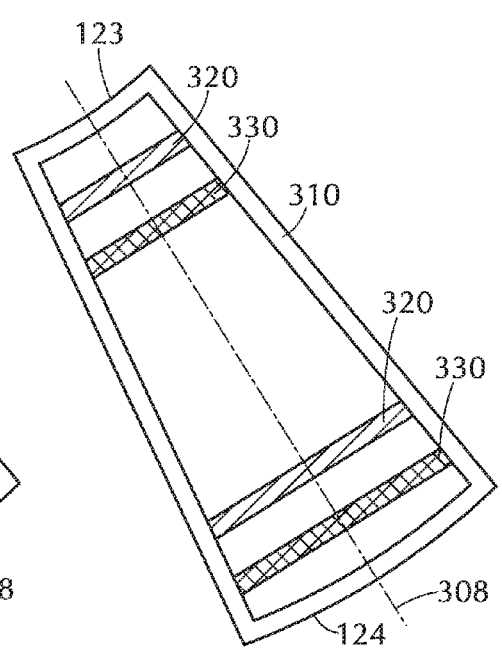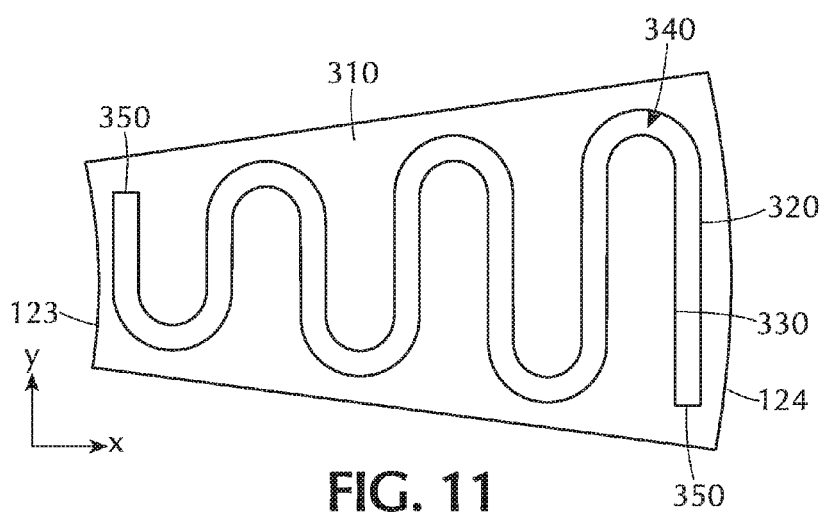

LATERAL PLASMA/RADICAL SOURCE

CROSS-REFERENCE TO RELATED APPLICATIONS

This application claims priority to U.S. Provisional Application No. 62/258,386, filed Nov. 20, 2015, the entire disclosure of which is hereby incorporated by reference herein.

FIELD

Embodiments of the disclosure generally relate to an apparatus for processing substrates. More particularly, embodiments of the disclosure relate to modular capacitively coupled plasma sources for use with processing chambers like batch processors.

BACKGROUND

Semiconductor device formation is commonly conducted in substrate processing platforms containing multiple chambers. In some instances, the purpose of a multi-chamber processing platform or cluster tool is to perform two or more processes on a substrate sequentially in a controlled environment. In other instances, however, a multiple chamber processing platform may only perform a single processing step on substrates; the additional chambers are intended to maximize the rate at which substrates are processed by the platform. In the latter case, the process performed on substrates is typically a batch process, wherein a relatively large number of substrates, e.g. 25 or 50, are processed in a given chamber simultaneously. Batch processing is especially beneficial for processes that are too time-consuming to be performed on individual substrates in an economically viable manner, such as for atomic layer deposition (ALD) processes and some chemical vapor deposition (CVD) processes.

Some ALD systems, especially spatial ALD systems with rotating substrate platens, benefit from a modular plasma source, i.e., a source that can be easily inserted into the system. The plasma source consists of a volume where plasma is generated, and a way to expose a workpiece to a flux of charged particles and active chemical radical species.

Thermal ALD and CVD processes frequently incorporate treatments for film quality enhancements. These treatments typically comprise energetic or reactive species. Plasma sources are a primary source for such species. Some concerns of plasma sources include energetic bombardment through ions and contamination of materials from the plasma source due to sputtering. There is a need for plasma sources that minimize contamination of the substrate by sputtered material while maintaining uniform plasma density.

SUMMARY

One or more embodiments of the disclosure are directed to plasma source assemblies comprising a housing, an RF hot electrode, and a return electrode. The housing has a gas inlet and the front face defining a flow path. The gas inlet allows the flow of gas to move along the flow path to pass through the housing and out the front face. The RF hot electrode is within the housing and has a first surface oriented substantially parallel to the flow path. The return electrode is within the housing and has a first surface oriented substantially parallel to the flow path and spaced from the first surface of the RF hot electrode to form a gap.

Additional embodiments of the disclosure are directed to processing chambers comprising a susceptor assembly and a gas distribution assembly. The susceptor assembly is within the processing chamber and has a top surface to support and rotate a plurality of substrates around a central axis. The gas distribution assembly has a front surface facing the top surface of the susceptor assembly to direct a flow of gases toward the top surface of the susceptor assembly. The guest distribution assembly includes a plasma source assembly comprising a wedge-shaped housing at least one RF hot electrode and at least one return electrode. The wedge-shaped housing has an inner peripheral end an outer peripheral end defining a major axis of the housing. The housing also has a first side, a second side, a gas inlet and a front face. The gas inlet and front face define a flow path and the gas inlet allows a flow of gas to move along the flow path to pass through the housing and out the front face. The at least one RF hot electrode is within the housing and has a first surface oriented substantially parallel to the flow path. The at least one return electrode is within the housing and has a first surface oriented substantially parallel to the flow path and spaced from the RF hot electrode to form a gap. The front face of the wedge-shaped housing of the plasma source assembly is positioned at a distance from the top surface of the susceptor assembly in the range of about 1 mm to about 5 mm.

Further embodiments of the disclosure are directed to methods of processing a substrate. A substrate is positioned on a susceptor assembly adjacent a gas distribution assembly. The gas distribution assembly includes a plasma source assembly comprising a wedge-shaped housing, at least one RF hot electrode and at least one return electrode. The wedge-shaped housing has an inner peripheral end and an outer peripheral end defining a major axis of the housing. The housing has a first side, a second side, a gas inlet and a front face. The gas inlet and front face define a flow path and the gas inlet allowing a flow of gas to move along the flow path to pass through the housing and out the front face. The at least one RF hot electrode is within the housing and has a first surface oriented substantially parallel to the flow path. The at least one return electrode is within the housing and has a first surface oriented substantially parallel to the flow path and spaced from the first surface of the RF hot electrode to form a gap. A gas if flowed through the gas inlet of the wedge-shaped housing into the gap between the RF hot electrode and the return electrode. The RF hot electrode is energized to form a plasma in the gap and the substrate is exposed to the plasma.

BRIEF DESCRIPTION OF THE DRAWINGS

So that the manner in which the above recited features of embodiments of the disclosure can be understood in detail, a more particular description of embodiments of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

FIGS. 10A and 10B show a schematic bottom views of plasma source assemblies in accordance with one or more embodiments of the disclosure;

FIG. 11 shows a schematic bottom view of a plasma source assembly with serpentine electrodes in accordance with one or more embodiments of the disclosure;

DETAILED DESCRIPTION

Figure 1:
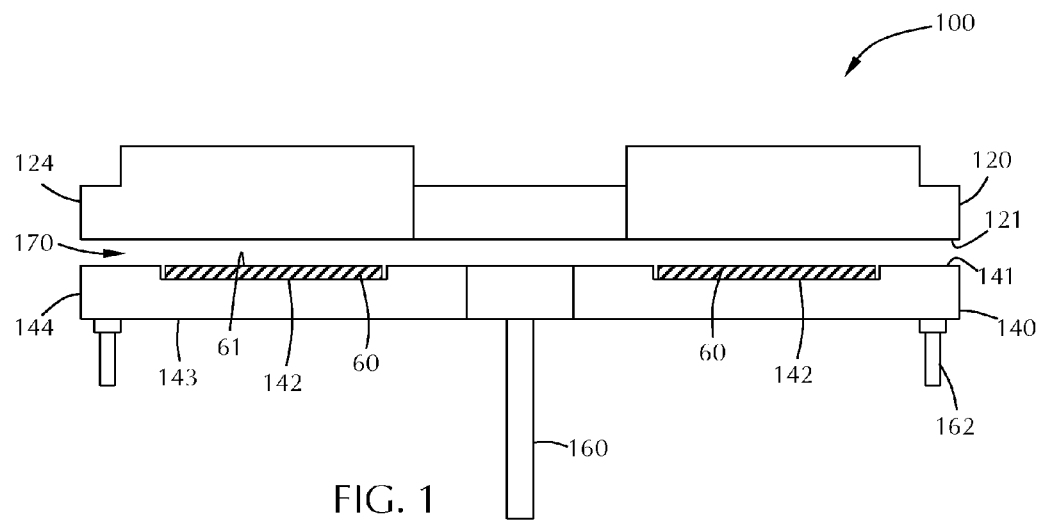
FIG. 1 shows a schematic cross-sectional view of a substrate processing system in accordance with one or more embodiments of the disclosure.

Embodiments of the disclosure provide a substrate processing system for continuous substrate deposition to maximize throughput and improve processing efficiency. The substrate processing system can also be used for pre-deposition and post-deposition plasma treatments.

As used in this specification and the appended claims, the term "substrate" and "wafer" are used interchangeably, both referring to a surface, or portion of a surface, upon which a process acts. It will also be understood by those skilled in the art that reference to a substrate can also refer to only a portion of the substrate, unless the context clearly indicates otherwise. Additionally, reference to depositing on a substrate can mean both a bare substrate and a substrate with one or more films or features deposited or formed thereon.

As used in this specification and the appended claims, the terms "reactive gas", "precursor", "reactant", and the like, are used interchangeably to mean a gas that includes a species which is reactive with a substrate surface. For example, a first "reactive gas" may simply adsorb onto the surface of a substrate and be available for further chemical reaction with a second reactive gas.

As used in this specification and the appended claims, the term "reduced pressure" means a pressure less than about 100 Torr, or less than about 75 Torr, or less than about 50 Torr, or less than about 25 Torr. For example, "medium pressure" defined as in the range of about 1 Torr to about 25 Torr is reduced pressure.

Rotating platen chambers are being considered for many applications. In such a chamber, one or more wafers are placed on a rotating holder ("platen"). As the platen rotates, the wafers move between various processing areas. For example, in ALD, the processing areas would expose the wafer to precursors and reactants. In addition, plasma exposure may be used as a reactant or to treat the film or the substrate surface for enhanced film growth or to modify film properties. Some embodiments of the disclosure provide for uniform deposition and post-treatment (e.g., densification) of ALD films when using a rotating platen ALD chamber.

Rotating platen ALD chambers can deposit films by traditional time-domain processes where the entire wafer is exposed to a first gas, purged and then exposed to the second gas, or by spatial ALD where portions of the wafer are exposed to the first gas and portions are exposed to the second gas and the movement of the wafer through these gas streams deposits the layer.

As used in this specification and the appended claims, the terms "pie-shaped" and "wedge-shaped" are used interchangeably to describe a body that is a generally circular sector. For example, a wedge-shaped segment may be a fraction of a circle or disc-shaped structure. The inner edge of the pie-shaped segment can come to a point or can be truncated to a flat edge or rounded. The path of the substrates can be perpendicular to the gas ports. In some embodiments, each of the gas injector assemblies comprises a plurality of elongate gas ports which extend in a direction substantially perpendicular to the path traversed by a substrate, where a front edge of the gas ports is substantially parallel to the platen. As used in this specification and the appended claims, the term "substantially perpendicular" means that the general direction of movement of the substrates is along a plane approximately perpendicular (e.g., about 45° to 90°) to the axis of the gas ports. For a wedge-shaped gas port, the axis of the gas port can be considered to be a line defined as the mid-point of the width of the port extending along the length of the port.

FIG. 1 shows a cross-section of a processing chamber 100 including a gas distribution assembly 120, also referred to as injectors or an injector assembly, and a susceptor assembly 140. The gas distribution assembly 120 is any type of gas delivery device used in a processing chamber. The gas distribution assembly 120 includes a front surface 121 which faces the susceptor assembly 140. The front surface 121 can have any number or variety of openings to deliver a flow of gases toward the susceptor assembly 140. The gas distribution assembly 120 also includes an outer peripheral edge 124 which in the embodiments shown, is substantially round.

The specific type of gas distribution assembly 120 used can vary depending on the particular process being used. Embodiments of the disclosure can be used with any type of processing system where the gap between the susceptor and the gas distribution assembly is controlled. While various types of gas distribution assemblies can be employed (e.g., showerheads), embodiments of the disclosure may be particularly useful with spatial ALD gas distribution assemblies which have a plurality of substantially parallel gas channels. As used in this specification and the appended claims, the term "substantially parallel" means that the elongate axis of the gas channels extend in the same general direction. There can be slight imperfections in the parallelism of the gas channels. The plurality of substantially parallel gas channels can include at least one first reactive gas A channel, at least one second reactive gas B channel, at least one purge gas P channel and/or at least one vacuum V channel. The gases flowing from the first reactive gas A channel(s), the second reactive gas B channel(s) and the purge gas P channel(s) are directed toward the top surface of the wafer. Some of the gas flow moves horizontally across the surface of the wafer and out of the processing region through the purge gas P channel(s). A substrate moving from one end of the gas distribution assembly to the other end will be exposed to each of the process gases in turn, forming a layer on the substrate surface.

Figure 2:
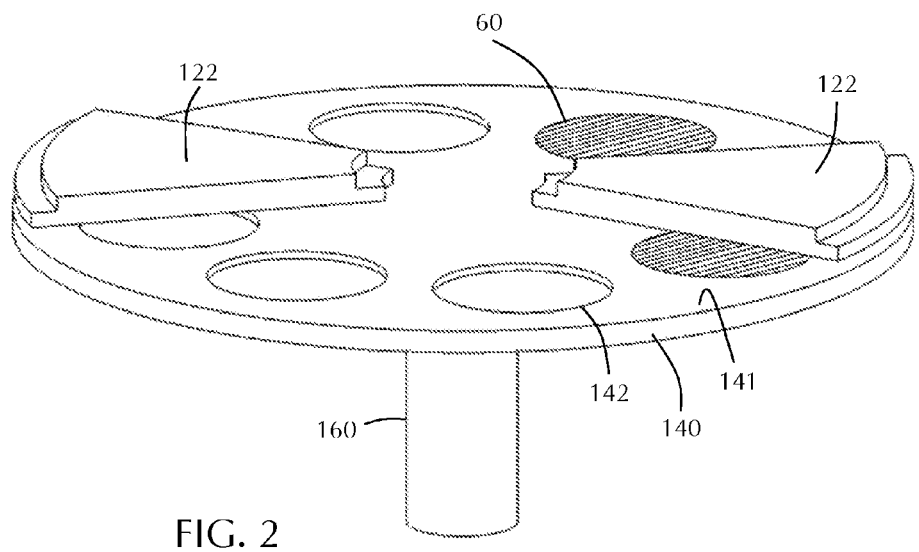
FIG. 2 shows a perspective view of a substrate processing system in accordance with one or more embodiment of the disclosure.

In some embodiments, the gas distribution assembly 120 is a rigid stationary body made of a single injector unit. In one or more embodiments, the gas distribution assembly 120 is made up of a plurality of individual sectors (e.g., injector units 122), as shown in FIG. 2. Either a single piece body or a multi-sector body can be used with the various embodiments of the disclosure described.

The susceptor assembly 140 is positioned beneath the gas distribution assembly 120. The susceptor assembly 140 includes a top surface 141 and at least one recess 142 in the top surface 141. The susceptor assembly 140 also has a bottom surface 143 and an edge 144. The recess 142 can be any suitable shape and size depending on the shape and size of the substrates 60 being processed. In the embodiment shown in FIG. 1, the recess 142 has a flat bottom to support the bottom of the wafer; however, the bottom of the recess can vary. In some embodiments, the recess has step regions around the outer peripheral edge of the recess which are sized to support the outer peripheral edge of the wafer. The amount of the outer peripheral edge of the wafer that is supported by the steps can vary depending on, for example, the thickness of the wafer and the presence of features already present on the back side of the wafer.

In some embodiments, as shown in FIG. 1, the recess 142 in the top surface 141 of the susceptor assembly 140 is sized so that a substrate 60 supported in the recess 142 has a top surface 61 substantially coplanar with the top surface 141 of the susceptor 140. As used in this specification and the appended claims, the term "substantially coplanar" means that the top surface of the wafer and the top surface of the susceptor assembly are coplanar within ±0.2 mm. In some embodiments, the top surfaces are coplanar within ±0.15 mm, ±0.10 mm or ±0.05 mm.

The susceptor assembly 140 of FIG. 1 includes a support post 160 which is capable of lifting, lowering and rotating the susceptor assembly 140. The susceptor assembly may include a heater, or gas lines, or electrical components within the center of the support post 160. The support post 160 may be the primary means of increasing or decreasing the gap between the susceptor assembly 140 and the gas distribution assembly 120, moving the susceptor assembly 140 into proper position. The susceptor assembly 140 may also include fine tuning actuators 162 which can make micro-adjustments to susceptor assembly 140 to create a predetermined gap 170 between the susceptor assembly 140 and the gas distribution assembly 120. In some embodiments, the gap 170 distance is in the range of about 0.1 mm to about 5.0 mm, or in the range of about 0.1 mm to about 3.0 mm, or in the range of about 0.1 mm to about 2.0 mm, or in the range of about 0.2 mm to about 1.8 mm, or in the range of about 0.3 mm to about 1.7 mm, or in the range of about 0.4 mm to about 1.6 mm, or in the range of about 0.5 mm to about 1.5 mm, or in the range of about 0.6 mm to about 1.4 mm, or in the range of about 0.7 mm to about 1.3 mm, or in the range of about 0.8 mm to about 1.2 mm, or in the range of about 0.9 mm to about 1.1 mm, or about 1 mm.

The processing chamber 100 shown in the Figures is a carousel-type chamber in which the susceptor assembly 140 can hold a plurality of substrates 60. As shown in FIG. 2, the gas distribution assembly 120 may include a plurality of separate injector units 122, each injector unit 122 being capable of depositing a film on the wafer, as the wafer is moved beneath the injector unit. Two pie-shaped injector units 122 are shown positioned on approximately opposite sides of and above the susceptor assembly 140. This number of injector units 122 is shown for illustrative purposes only. It will be understood that more or less injector units 122 can be included. In some embodiments, there are a sufficient number of pie-shaped injector units 122 to form a shape conforming to the shape of the susceptor assembly 140. In some embodiments, each of the individual pie-shaped injector units 122 may be independently moved, removed and/or replaced without affecting any of the other injector units 122. For example, one segment may be raised to permit a robot to access the region between the susceptor assembly 140 and gas distribution assembly 120 to load/unload substrates 60.

Figure 3:
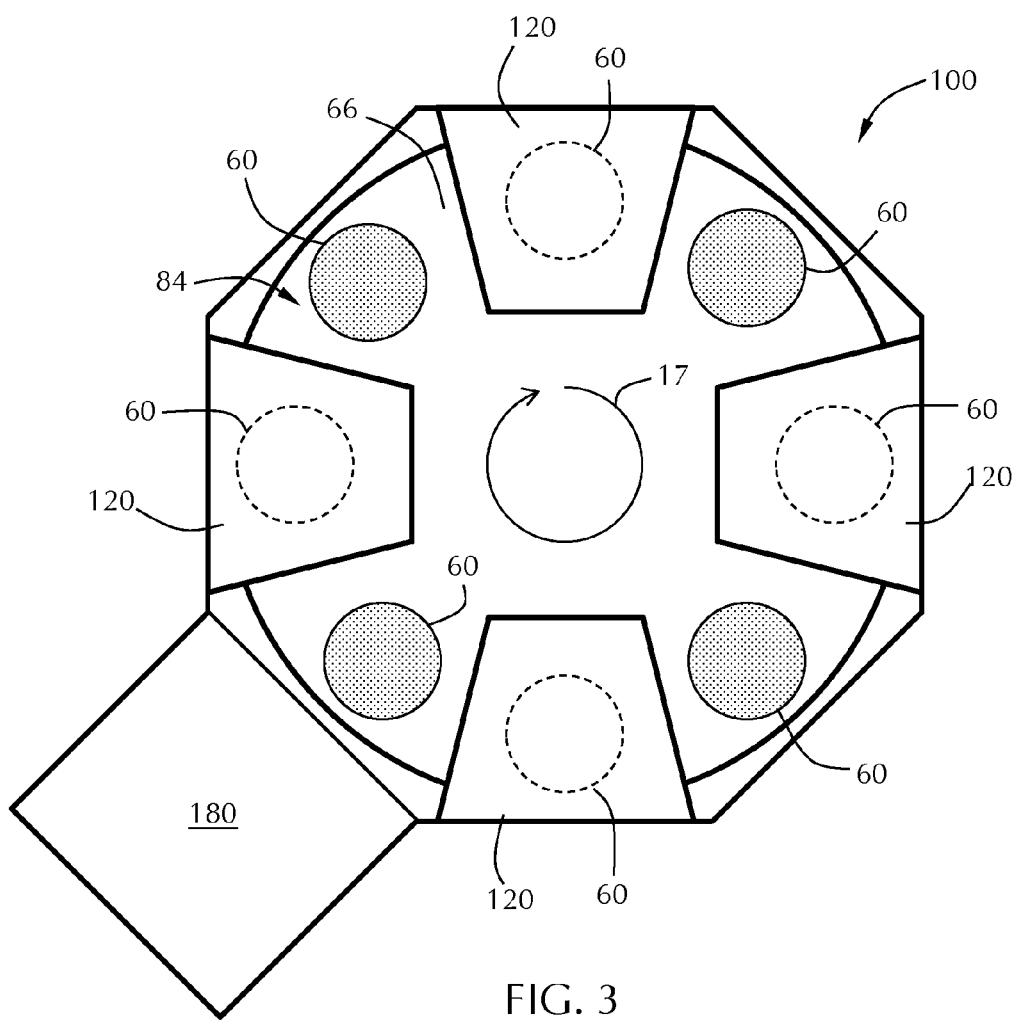
FIG. 3 shows a schematic of a substrate processing system in accordance with one or more embodiment of the disclosure.

Processing chambers having multiple gas injectors can be used to process multiple wafers simultaneously so that the wafers experience the same process flow. For example, as shown in FIG. 3, the processing chamber 100 has four gas injector assemblies and four substrates 60. At the outset of processing, the substrates 60 can be positioned between the injector assemblies 30. Rotating 17 the susceptor assembly 140 by 45° will result in each substrate 60 which is between gas distribution assemblies 120 to be moved to an gas distribution assembly 120 for film deposition, as illustrated by the dotted circle under the gas distribution assemblies 120. An additional 45° rotation would move the substrates 60 away from the injector assemblies 30. With spatial ALD injectors, a film is deposited on the wafer during movement of the wafer relative to the injector assembly. In some embodiments, the susceptor assembly 140 is rotated in increments that prevent the substrates 60 from stopping beneath the gas distribution assemblies 120. The number of substrates 60 and gas distribution assemblies 120 can be the same or different. In some embodiments, there is the same number of wafers being processed as there are gas distribution assemblies. In one or more embodiments, the number of wafers being processed are fraction of or an integer multiple of the number of gas distribution assemblies. For example, if there are four gas distribution assemblies, there are 4× wafers being processed, where x is an integer value greater than or equal to one.

The processing chamber 100 shown in FIG. 3 is merely representative of one possible configuration and should not be taken as limiting the scope of the disclosure. Here, the processing chamber 100 includes a plurality of gas distribution assemblies 120. In the embodiment shown, there are four gas distribution assemblies (also called injector assemblies 30) evenly spaced about the processing chamber 100. The processing chamber 100 shown is octagonal, however, those skilled in the art will understand that this is one possible shape and should not be taken as limiting the scope of the disclosure. The gas distribution assemblies 120 shown are trapezoidal, but can be a single circular component or made up of a plurality of pie-shaped segments, like that shown in FIG. 2.

The embodiment shown in FIG. 3 includes a load lock chamber 180, or an auxiliary chamber like a buffer station.

This chamber 180 is connected to a side of the processing chamber 100 to allow, for example the substrates (also referred to as substrates 60) to be loaded/unloaded from the processing chamber 100. A wafer robot may be positioned in the chamber 180 to move the substrate onto the susceptor.

Rotation of the carousel (e.g., the susceptor assembly 140) can be continuous or discontinuous. In continuous processing, the wafers are constantly rotating so that they are exposed to each of the injectors in turn. In discontinuous processing, the wafers can be moved to the injector region and stopped, and then to the region 84 between the injectors and stopped. For example, the carousel can rotate so that the wafers move from an inter-injector region across the injector (or stop adjacent the injector) and on to the next inter-injector region where the carousel can pause again. Pausing between the injectors may provide time for additional processing steps between each layer deposition (e.g., exposure to plasma).

Figure 4:
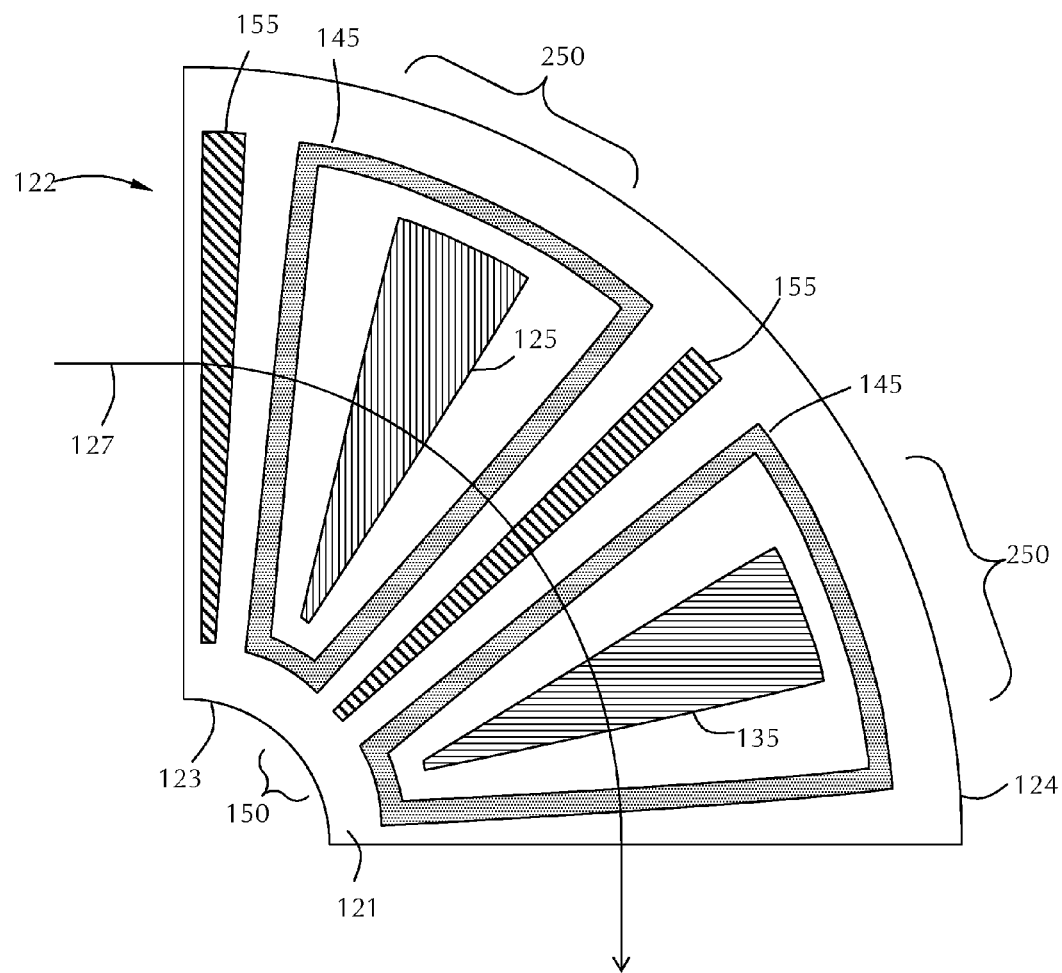
FIG. 4 shows a schematic view of a front of a gas distribution assembly in accordance with one or more embodiment of the disclosure.
Figure 5:
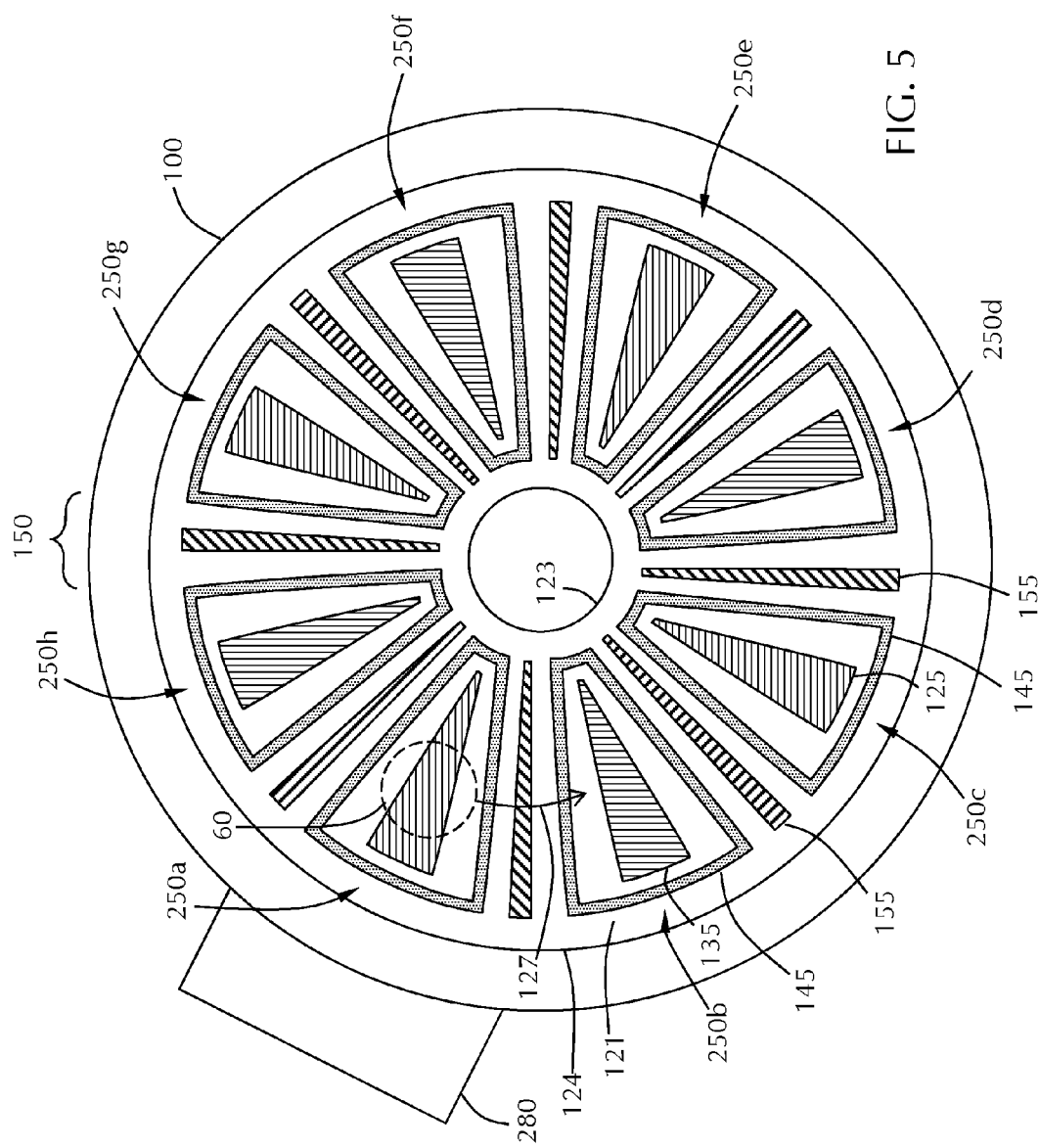
FIG. 5 shows a schematic view of a processing chamber in accordance with one or more embodiment of the disclosure.

FIG. 4 shows a sector or portion of a gas distribution assembly 220, which may be referred to as an injector unit 122. The injector units 122 can be used individually or in combination with other injector units. For example, as shown in FIG. 5, four of the injector units 122 of FIG. 4 are combined to form a single gas distribution assembly 220. (The lines separating the four injector units are not shown for clarity.) While the injector unit 122 of FIG. 4 has both a first reactive gas port 125 and a second reactive gas port 135 in addition to purge gas ports 155 and vacuum ports 145, an injector unit 122 does not need all of these components.

Referring to both FIGS. 4 and 5, a gas distribution assembly 220 in accordance with one or more embodiment may comprise a plurality of sectors (or injector units 122) with each sector being identical or different. The gas distribution assembly 220 is positioned within the processing chamber and comprises a plurality of elongate gas ports 125, 135, 145, 155 in a front surface 121 of the gas distribution assembly 220. The plurality of elongate gas ports 125, 135, 145, 155 extend from an area adjacent the inner peripheral edge 123 toward an area adjacent the outer peripheral edge 124 of the gas distribution assembly 220. The plurality of gas ports shown include a first reactive gas port 125, a second reactive gas port 135, a vacuum port 145 which surrounds each of the first reactive gas ports and the second reactive gas ports and a purge gas port 155.

With reference to the embodiments shown in FIG. 4 or 5, when stating that the ports extend from at least about an inner peripheral region to at least about an outer peripheral region, however, the ports can extend more than just radially from inner to outer regions. The ports can extend tangentially as vacuum port 145 surrounds reactive gas port 125 and reactive gas port 135. In the embodiment shown in FIGS. 4 and 5, the wedge shaped reactive gas ports 125, 135 are surrounded on all edges, including adjacent the inner peripheral region and outer peripheral region, by a vacuum port 145.

Referring to FIG. 4, as a substrate moves along path 127, each portion of the substrate surface is exposed to the various reactive gases. To follow the path 127, the substrate will be exposed to, or "see", a purge gas port 155, a vacuum port 145, a first reactive gas port 125, a vacuum port 145, a purge gas port 155, a vacuum port 145, a second reactive gas port 135 and a vacuum port 145. Thus, at the end of the path 127 shown in FIG. 4, the substrate has been exposed to gas streams from the first reactive gas port 125 and the second reactive gas port 135 to form a layer. The injector unit 122 shown makes a quarter circle but could be larger or smaller.

The gas distribution assembly 220 shown in FIG. 5 can be considered a combination of four of the injector units 122 of FIG. 4 connected in series.

The injector unit 122 of FIG. 4 shows a gas curtain 150 that separates the reactive gases. The term "gas curtain" is used to describe any combination of gas flows or vacuum that separate reactive gases from mixing. The gas curtain 150 shown in FIG. 4 comprises the portion of the vacuum port 145 next to the first reactive gas port 125, the purge gas port 155 in the middle and a portion of the vacuum port 145 next to the second reactive gas port 135. This combination of gas flow and vacuum can be used to prevent or minimize gas phase reactions of the first reactive gas and the second reactive gas.

Referring to FIG. 5, the combination of gas flows and vacuum from the gas distribution assembly 220 form a separation into a plurality of processing regions 250. The processing regions are roughly defined around the individual reactive gas ports 125, 135 with the gas curtain 150 between 250. The embodiment shown in FIG. 5 makes up eight separate processing regions 250 with eight separate gas curtains 150 between. A processing chamber can have at least two processing region. In some embodiments, there are at least three, four, five, six, seven, eight, nine, 10, 11 or 12 processing regions.

During processing a substrate may be exposed to more than one processing region 250 at any given time. However, the portions that are exposed to the different processing regions will have a gas curtain separating the two. For example, if the leading edge of a substrate enters a processing region including the second reactive gas port 135, a middle portion of the substrate will be under a gas curtain 150 and the trailing edge of the substrate will be in a processing region including the first reactive gas port 125.

A factory interface 280, which can be, for example, a load lock chamber, is shown connected to the processing chamber 100. A substrate 60 is shown superimposed over the gas distribution assembly 220 to provide a frame of reference. The substrate 60 may often sit on a susceptor assembly to be held near the front surface 121 of the gas distribution assembly 120 (also referred to as a gas distribution plate). The substrate 60 is loaded via the factory interface 280 into the processing chamber 100 onto a substrate support or susceptor assembly (see FIG. 3). The substrate 60 can be shown positioned within a processing region because the substrate is located adjacent the first reactive gas port 125 and between two gas curtains 150a, 150b. Rotating the substrate 60 along path 127 will move the substrate counter-clockwise around the processing chamber 100. Thus, the substrate 60 will be exposed to the first processing region 250a through the eighth processing region 250h, including all processing regions between. For each cycle around the processing chamber, using the gas distribution assembly shown, the substrate 60 will be exposed to four ALD cycles of first reactive gas and second reactive gas.

The conventional ALD sequence in a batch processor, like that of FIG. 5, maintains chemical A and B flow respectively from spatially separated injectors with pump/purge section between. The conventional ALD sequence has a starting and ending pattern which might result in non-uniformity of the deposited film. The inventors have surprisingly discovered that a time based ALD process performed in a spatial ALD batch processing chamber provides a film with higher uniformity. The basic process of exposure to gas A, no reactive gas, gas B, no reactive gas would be to sweep the substrate under the injectors to saturate the surface with chemical A and B respectively to avoid having a starting and ending pattern form in the film. The inventors have surprisingly found that the time based approach is especially beneficial when the target film thickness is thin (e.g., less than 20 ALD cycles), where starting and ending pattern have a significant impact on the within wafer uniformity performance. The inventors have also discovered that the reaction process to create SiCN, SiCO and SiCON films, as described herein, could not be accomplished with a time-domain process. The amount of time used to purge the processing chamber results in the stripping of material from the substrate surface. The stripping does not happen with the spatial ALD process described because the time under the gas curtain is short.

Accordingly, embodiments of the disclosure are directed to processing methods comprising a processing chamber 100 with a plurality of processing regions 250a-250h with each processing region separated from an adjacent region by a gas curtain 150. For example, the processing chamber shown in FIG. 5. The number of gas curtains and processing regions within the processing chamber can be any suitable number depending on the arrangement of gas flows. The embodiment shown in FIG. 5 has eight gas curtains 150 and eight processing regions 250a-250h. The number of gas curtains is generally equal to or greater than the number of processing regions. For example, if region 250a had no reactive gas flow, but merely served as a loading area, the processing chamber would have seven processing regions and eight gas curtains.

A plurality of substrates 60 are positioned on a substrate support, for example, the susceptor assembly 140 shown FIGS. 1 and 2. The plurality of substrates 60 are rotated around the processing regions for processing. Generally, the gas curtains 150 are engaged (gas flowing and vacuum on) throughout processing including periods when no reactive gas is flowing into the chamber.

A first reactive gas A is flowed into one or more of the processing regions 250 while an inert gas is flowed into any processing region 250 which does not have a first reactive gas A flowing into it. For example if the first reactive gas is flowing into processing regions 250b through processing region 250h, an inert gas would be flowing into processing region 250a. The inert gas can be flowed through the first reactive gas port 125 or the second reactive gas port 135.

The inert gas flow within the processing regions can be constant or varied. In some embodiments, the reactive gas is co-flowed with an inert gas. The inert gas will act as a carrier and diluent. Since the amount of reactive gas, relative to the carrier gas, is small, co-flowing may make balancing the gas pressures between the processing regions easier by decreasing the differences in pressure between adjacent regions.

Some embodiments of the disclosure are directed to injector modules. While the injector modules are described with respect to a spatial ALD processing chamber, those skilled in the art will understand that the modules are not limited to spatial ALD chambers and can be applicable to any injector situation where increasing gas flow uniformity is useful.

Some embodiments of the disclosure advantageously provide modular plasma source assemblies, i.e., a source that can be easily inserted into and removed from the processing system. Such a source may have all or most of its hardware operating at the same pressure level as the atomic layer deposition process, typically 1-50 Torr. Some embodiments of the disclosure provide plasma sources with improved ion flux across the wafer surface. In some embodiments, plasma sources include a capacitive source between three plates aligned substantially perpendicular to the wafer surface. In some embodiments, the outer plates are grounded and the inner plate is powered. A plasma can be created between the plates while the gas species flows between the plates toward the wafer surface. The plasma is substantially confined to the source and minimizes sputtered material from the powered plate reaching the wafer surface. Some embodiments of the disclosure advantageously provide a plasma source that minimizes or eliminates contamination of the substrate by material sputtered from the hot electrode. Some embodiments also advantageously provide a soft plasma that does not substantially change of the substrate surface. One or more embodiments provide an apparatus that can generate a plasma without allowing the electrical return path to go through the substrate.

The gap between the RF hot electrode (the powered electrode) and the ground plate (referred to as a return electrode) can be varied. In some embodiments, the gap is in the range of about 4 mm to about 15 mm and may be adjustable. The width of the RF hot electrode can be varied. For example, the plates can be tapered to accelerate ions. In use, the gaseous species flowing in the gap between the RF hot electrode and the return electrode become ionized. The ionized species can then contact the substrate surface. The plasma formed by the various embodiments is a soft plasma that does not substantially change the substrate surface.

Referring to FIGS. 6 through 15, one or more embodiments of the disclosure are directed to modular capacitively coupled plasma sources 300. As used in this specification and the appended claims, the term "modular" means that plasma source 300 can be attached to or removed from a processing chamber. A modular source can generally be moved, removed or attached by a single person.

Figure 6:
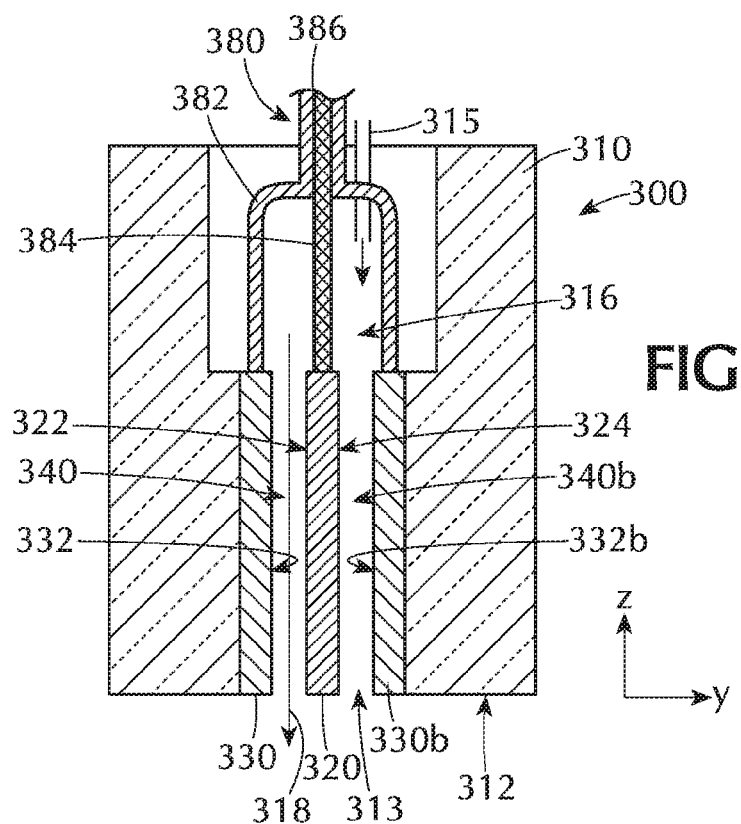
FIG. 6 shows a schematic cross-sectional view of a plasma source assembly in accordance with one or more embodiment of the disclosure.

FIG. 6 shows a cross-section of a plasma source assembly 300 in accordance with one or more embodiment of the disclosure. The plasma source assembly 300 shown in FIG. 6 includes a housing 310 with a gas inlet 315 and a front face 312. The gas inlet 315 allows a flow of gas to move along the flow path 318 through the housing 310 and out an opening 313 in the front face 312. The embodiment shown has a gas inlet 315 illustrated off-center for descriptive purposes, but those skilled in the art will understand that the gas inlet 315 can be centered in the housing 310. Additionally, some embodiments include a plenum 316 to increase the uniformity of the gas flow through the flow path 318.

The plasma source assembly 300 includes an RF hot electrode 320 and at least one return electrode 330. The return electrode 330 is any conductive material that forms a complete circuit with the RF hot electrode 320. Those skilled in the art will understand that the return electrode 330 can provide a pathway for electrons to flow. The term "return" used in this manner means that the electrode is part of the electrical pathway of the plasma components and does not imply a direction for the flow of current or electrons.

Figure 7:
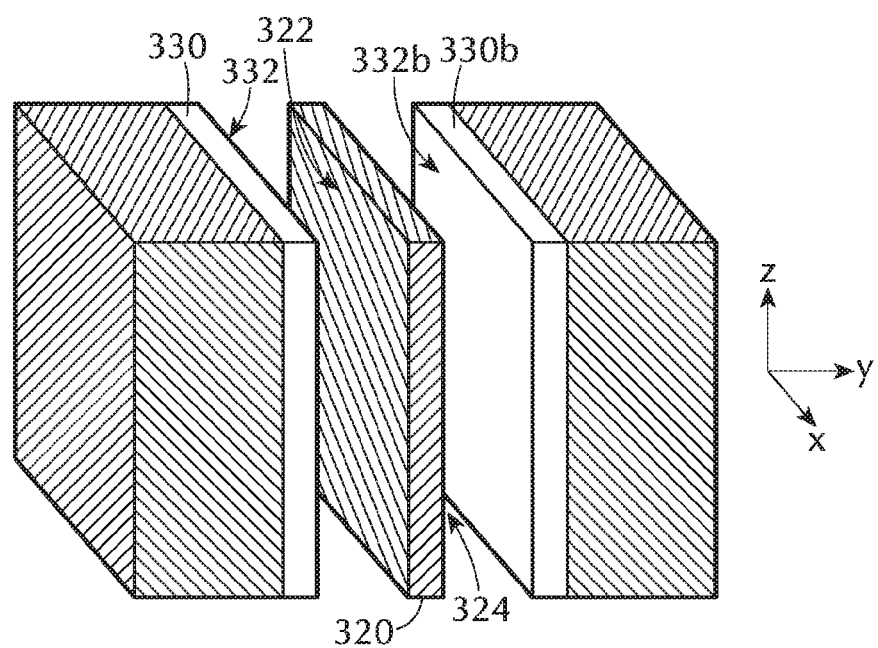
FIG. 7 shows a partial perspective view of a plasma source assembly in accordance with one or more embodiments of the disclosure.
Figure 8:
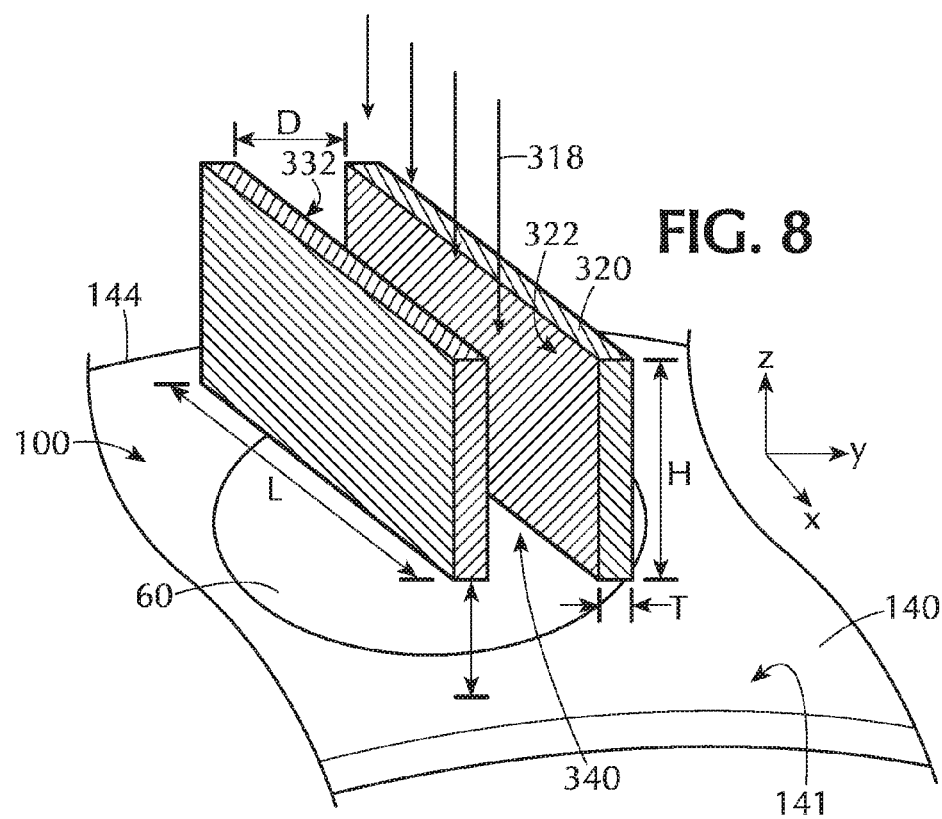
FIG. 8 shows a partial perspective view of a plasma source assembly in accordance with one or more embodiments of the disclosure.

Referring to FIGS. 6 to 8, the RF hot electrode 320 has a first surface 322 and a second surface 324 opposite the first surface 322. FIG. 6 shows a cross-section of a plasma source assembly 300 while FIGS. 7 and 8 show partial perspective views of the electrodes. As used in this regard, the first surface 322 and second surface 324 are on opposite sides of the thickness T of the RF hot electrode 320. The RF hot electrode 320 is a generally shaped as a rectangular prism with a height H, thickness T and length L. The RF hot electrode 320 has a first surface 322 oriented substantially parallel to the flow path 318. As used in this regard, the term "substantially parallel" means that the surface is within ±10° of parallel (defined as 0°).

The return electrode 330 is similarly shaped to the RF hot electrode 320. The return electrode has a first surface 332 that is oriented substantially parallel to the flow path 318. The first surface 332 of the return electrode 330 is spaced from the first surface 322 of the RF hot electrode 320 to form a gap 340.

The return electrode 330, 330b can be any suitable material including, but not limited to, aluminum, stainless steel and copper. The return electrode 330, 330b can have any suitable electrical characteristics. In some embodiments, the return electrode 330, 330b is a ground electrode. A ground electrode is any conductive material in electrical contact with electrical ground.

In some embodiments, the return electrode 330, 330b is a powered electrode different from the RF hot electrode 320. As used in this manner, "different from the RF hot electrode" means that the electrical properties or potential are different from the RF hot electrode. For example, the driving power of the generated plasma may be tuned in a push-pull manner from a single source using a phase shifter to minimize interaction with the wafer. In embodiments of this sort, the RF hot electrode 320 may be, for example, 180° out of phase with the return electrode 330.

As shown in FIG. 7, some embodiments of the plasma source assembly further comprise a second return electrode 330b. The second return electrode 330b has a first surface 332b which is oriented substantially parallel to the flow path 318. The first surface 332b of the second return electrode 330b is spaced from a second surface 324 of the RF hot electrode 320 to form a gap 340b. The gap 340 and gap 340b can have the same or different dimensions. In some embodiments, the gap 340, 340b between the RF hot electrode 320 and the return electrode 330, 330b is in the range of about 4 mm to about 15 mm, or in the range of about 5 mm to about 14 mm, or in the range of about 7 mm to about 13 mm, or in the range of about 9 mm to about 12 mm, or about 11 mm.

Figure 9:
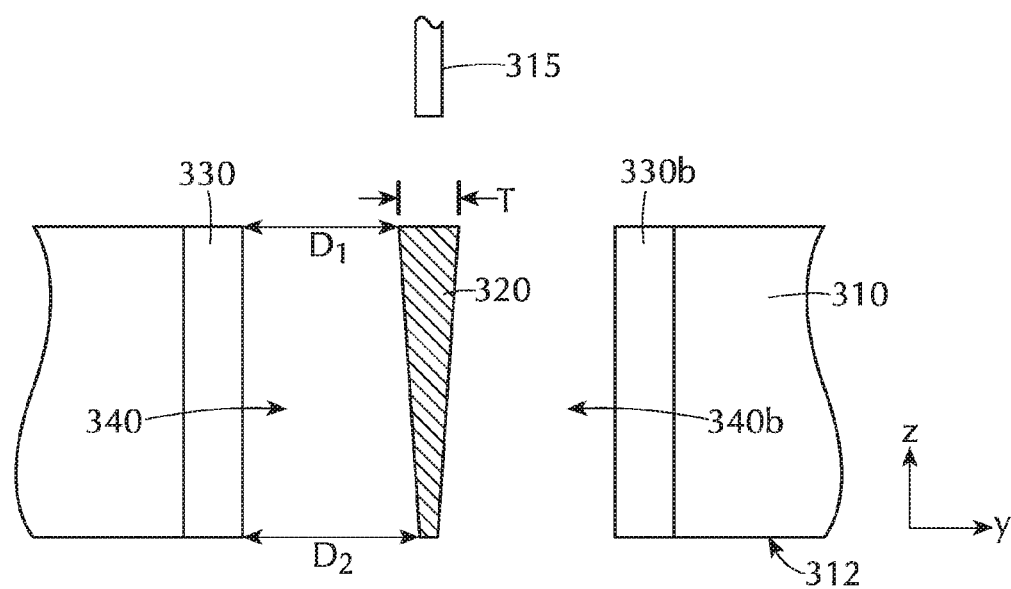
FIG. 9 shows a partial schematic side view of a plasma source assembly in accordance with one or more embodiments of the disclosure.

Referring to FIG. 9, in some embodiments the gap 340, 340b between the RF hot electrode 320 and the return electrode 330, 330b changes along the height H of the electrodes. In the embodiment shown, the thickness T is greater adjacent the gas inlet 315 than adjacent the front face 312. Stated different the size of the gap 340, 340b is smaller adjacent the gas inlet 315 than adjacent the front face 312. Without being bound by any particular theory of operation, it is believed that the tapered thickness of the RF hot electrode 320 may cause ions to the accelerated towards the wafer.

The thickness T of the RF hot electrode 320 can be any suitable thickness depending on, for example, the electrode material. In some embodiments, the RF hot electrode has a thickness in the range of about 3 mm to about 11 mm, or in the range of about 4 mm to about 10 mm, or in the range of about 6 mm to about 9 mm or about 8 mm.

The height H of the RF hot electrode 320 can be varied. In some embodiments, the height H of the RF hot electrode 320 is in the range of about 8 mm to about 40 mm, or in the range of about 9 mm to about 35 mm, or in the range of about 10 mm to about 30 mm, or in the range of about 11 mm to about 25 mm, or in the range of about 12 mm to about 20 mm, or in the range of about 13 mm to about 15 mm or about 14 mm.

In some embodiments, the housing 310 of the plasma source assembly 300 is wedge-shaped. FIGS. 10A and 10B show two embodiments incorporating wedge-shaped housings 310. In FIG. 10A, the RF hot electrode 320 and the return electrode 330 extend along a major axis 308 of the housing 310. The major axis 308, as used in this manner, refers to the axis between the middle of the inner peripheral edge 123 and the outer peripheral edge 124 of the housing 310. In FIG. 10B, the RF hot electrodes 320 and the return electrodes 330 extend perpendicular to the major axis 308 of the housing 310.

The spacing between the RF hot electrodes 320 and the return electrodes 330 can be substantially the same throughout the plasma source assembly or can vary. For example, in some embodiments, the RF hot electrode and the return electrode are spaced further apart at the outer peripheral edge 124 of the wedge-shaped housing 310 than near the inner peripheral edge 123.

FIG. 11 shows another embodiment of the disclosure in which the RF hot electrode 320 has a serpentine shape within the housing 310. As used in this regard, the term "serpentine shape" means that the electrode has a winding shape. The shape can conform to the shape of the housing 310. For example, the housing 310 of FIG. 11 is wedge-shaped and the RF hot electrode 320 has a serpentine shape that is larger near the outer peripheral edge 124 than near the inner peripheral edge 123. The return electrode 330 has a complementary shape to the RF hot electrode 320 to maintain substantially the same gap 340 along the length of the serpentine shape. As used in this regard, the term "substantially the same gap" means that the gap along the entire length does not vary by more than 10% of the average gap. An end dielectric 350 can be positioned between the RF hot electrode 320 and the return electrode 330. The end dielectric 350 can be any suitable material that can minimize electrical connection between the RF hot electrode 320 and the return electrode 330.

Figure 12:
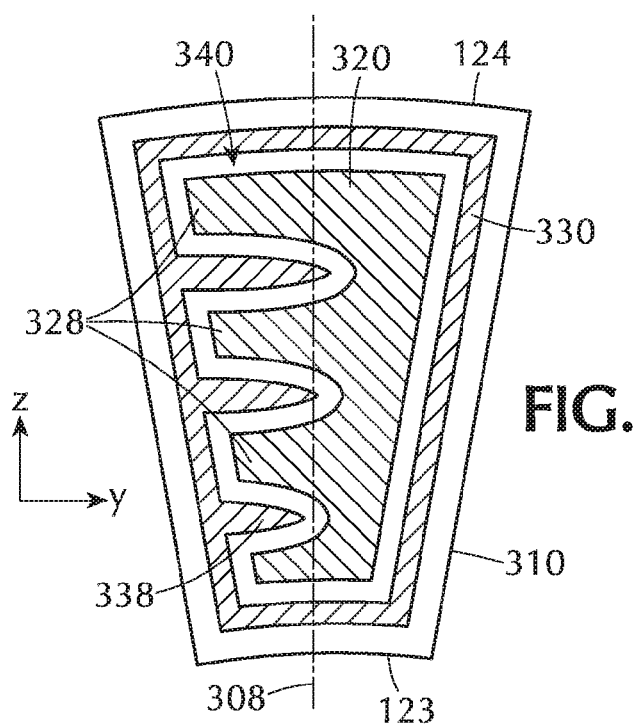
FIG. 12 shows a schematic bottom view of a plasma source assembly in accordance with one or more embodiments of the disclosure.

FIG. 12 shows another embodiment of the disclosure in which the RF hot electrode 320 has a plurality of fingers 328 extending perpendicular to a major axis 308 of the housing 310. While the embodiment shown has four fingers 328, those skilled in the art will understand that the RF hot electrode 320 can have any suitable number of fingers 328 depending on, for example, the size of the housing 310. The return electrode 330 has a shape that is complementary to the RF hot electrode 320 so that there is a plurality of fingers 338 on the return electrode 330. In some embodiments, the return electrode 330 is shaped to maintain substantially the same gap between the RF hot electrode 320 and the return electrode 330. The wedge-shaped housing 310 shown in FIG. 12 has a gap near the innermost finger 328 and the outermost finger 328 that is larger than the gap near the intermediate fingers. This variation may be due to the shape of the housing 310 or to control the plasma density at these regions.

Figure 13:
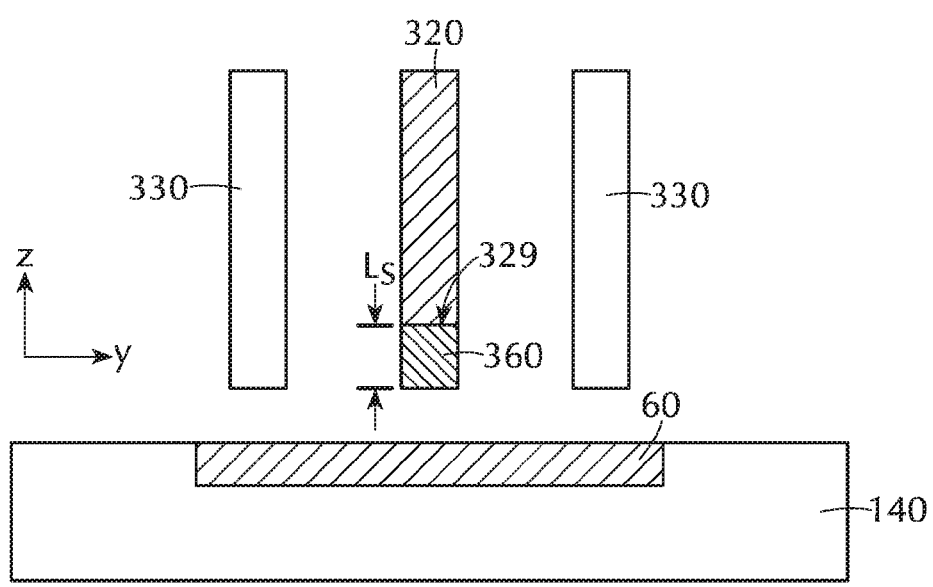
FIG. 13 shows a partial cross-sectional side schematic of plasma source assembly electrodes in accordance with one or more embodiment of the disclosure.

Some embodiments include a spacer 360 adjacent a lower edge 329 of the RF hot electrode 320. Referring to FIG. 13, the RF hot electrode 320 is illustrated between two return electrodes 330. A spacer 360 separates the lower edge 329 of the RF hot electrode 320 from the substrate 60 and susceptor assembly 140. The presence of the spacer 360, in some embodiments, help prevent or minimize sputtering of the RF hot electrode 320 from contaminating the substrate 60. The spacer 360 can be made of any suitable material including, but not limited to, dielectrics (e.g., ceramic materials). The size of the spacer 360 can be adjusted to move the lower edge 329 of the RF hot electrode 320 from the vicinity of the substrate 60. In some embodiments, the spacer 360 has a length Ls in the range of about 10 mm to about 25 mm, or in the range of about 13 mm to about 20 mm or about 17 mm.

Figure 14:
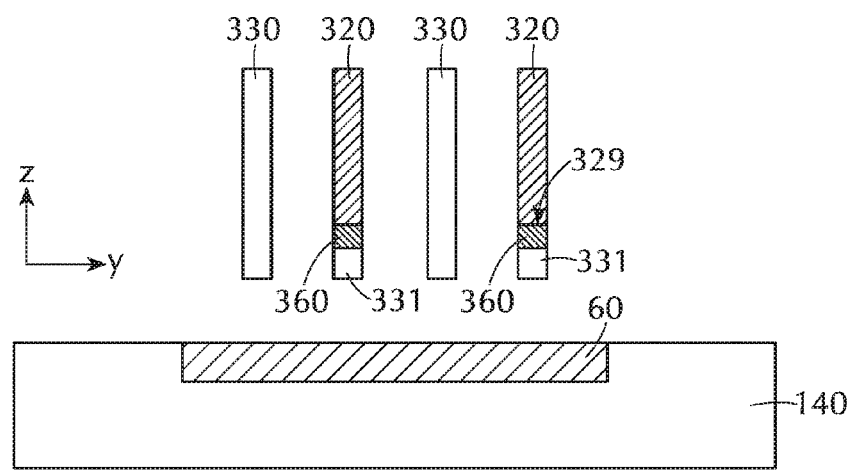
FIG. 14 shows a partial cross-sectional side schematic of a plasma source assembly electrodes in accordance with one or more embodiment of the disclosure.

FIG. 14 shows another embodiment of the disclosure. The RF hot electrodes 320 have a spacer 360 adjacent the lower edge 329. A return electrode 331 (e.g., ground or powered)

is adjacent the spacer 360 separating the spacer from the substrate 60 and susceptor assembly. Without being bound by any particular theory of operation, it is believed that the combination of the spacer 360 and return electrode 331 minimizes direct interaction of the RF hot electrode 320 with the substrate. Although two RF hot electrodes 320 and two return electrodes 330 are illustrated in FIG. 14, those skilled in the art will understand that there can by any suitable number of RF hot electrodes 320 and return electrodes 330.

Figure 15:
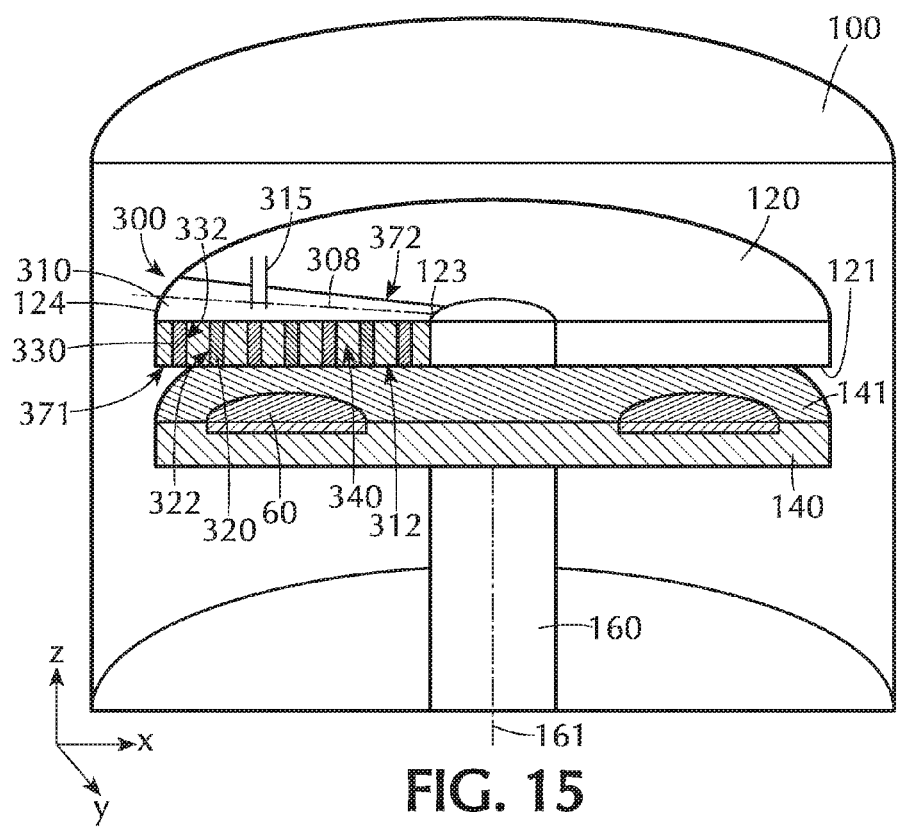
FIG. 15 shows a cross-sectional view of a processing chamber in accordance with one or more embodiments of the disclosure.

Referring to FIGS. 1, 2, 8 and 15, some embodiments of the disclosure are directed to processing chambers 100 including a susceptor assembly 140 and a gas distribution assembly 120. FIG. 15 shows a cross-sectional view of a processing chamber 100 in accordance with one or more embodiments of the disclosure. The susceptor assembly 140 has a top surface 141 to support and rotate a plurality of substrates 60 around a central axis 161.

The gas distribution assembly 120 has a front surface 121 facing the top surface 141 of the susceptor assembly 140 to direct a flow of gases toward the top surface 141 of the susceptor assembly 140. The gas distribution assembly 120 of some embodiments includes a plasma source assembly 300 with a wedge-shaped housing 310. The wedge-shaped housing has an inner peripheral edge 123 and an outer peripheral edge 124 defining a major axis 308 of the housing 310. The housing 310 has a first side 371, a second side 372, a gas inlet 315 and a front face 312. A flow path is defined as the path followed by a gas flowing from the gas inlet 315 through the housing 310 and exiting from the front face 312.

The plasma source assembly 300 has at least one RF hot electrode 320 with a first surface 322 oriented substantially parallel to the flow path. In the embodiment shown, there are three RF hot electrodes 320. At least one return electrode 330 is within the housing 310 and has a first surface 332 oriented parallel to the flow path and spaced from the first surface 322 of the RF hot electrode 320 to form a gap 340. The front face 312 of the wedge-shaped housing 310 of the plasma source assembly 300 is positioned a distance from the top surface 141 of the susceptor assembly 140 in the range of about 1 mm to about 5 mm, or in the range of about 1.5 mm to about 4 mm, or about 2 mm. The embodiment shown in FIG. 15 is merely exemplary of one possible configuration of a processing chamber with a plasma source assembly and should not be taken as limiting the scope of the disclosure.

Referring back to FIG. 6, some embodiments include a coaxial RF feed line 380 that passes through the housing 310 and provides power for the RF hot electrode 320 to generate the plasma in the gap 340. The coaxial RF feed line 380 includes an outer conductor 382 and an inner conductor 384 separated by an insulator 386. The inner conductor 384 is in electrical communication with the RF hot electrode 320 and outer conductor 382 is in electrical communication with electrical ground or a different phase power source than the RF hot electrode. As used in this specification and the appended claims, the term "electrical communication" means that the components are connected either directly or through an intermediate component so that there is little electrical resistance.

The coaxial RF feed line 380 may be constructed so that the outer conductor 382 terminates on the return electrode 330. The inner conductor 384 can terminate on the RF hot electrode 320. In some embodiments, the gas inlet 315 is fed to the housing around the outside periphery of the coaxial feed. The RF feed may be in the form of a coaxial transmission line. The outer conductor can be connected/terminated in the return electrode, and the inner conductor is connected to the RF hot electrode. The return electrode 330 can be connected to the metal housing by any suitable method including, but not limited to, a metal gasket. This helps to ensure a symmetric geometry of the return currents. All return currents flow up the outer conductor of the feed, minimizing RF noise. In some embodiments, the RF feed is designed to provide symmetric RF feed current to the RF hot electrode, and symmetric return currents. All return currents flow up the outer conductor, minimizing RF noise, and minimizing impact of source installation on operation.

Additional embodiments of the disclosure are directed to methods of processing a substrate. A generic method is described with respect to the embodiment of FIG. 15, but it will be understood that the plasma source assembly can be any embodiment or combination of embodiments described. A substrate 60 is positioned on a susceptor assembly 140 adjacent a gas distribution assembly 120. The gas distribution assembly 120 includes a plasma source assembly in accordance with one or more embodiments of the disclosure. A gas is flowed through the gas inlet 315 of the wedge-shaped housing 310 into the gap 340 between the RF hot electrode 320 and the return electrode 330. The RF hot electrode 320 is energized to form a plasma in the gap 340. The plasma flows out the front face 312 of the housing 310 to expose the substrate 60 to the plasma.

Some embodiments of the disclosure are directed to processing chambers comprising at least one capacitively coupled wedge-shaped plasma source 100 positioned along an arcuate path in a processing chamber. As used in this specification and the appended claims, the term "arcuate path" means any path which travels at least a portion of a circular-shaped or an oval-shaped path. The arcuate path can include the movement of the substrate along a portion of the path of at least about 5°, 10°, 15°, 20°, Additional embodiments of the disclosure are directed to methods of processing a plurality of substrates. The plurality of substrates is loaded onto substrate support in a processing chamber. The substrate support is rotated to pass each of the plurality of substrates across a gas distribution assembly to deposit a film on the substrate. The substrate support is rotated to move the substrates to a plasma region adjacent a capacitively coupled wedge-shaped plasma source generating substantially uniform plasma in the plasma region. This is repeated until a film of predetermined thickness is formed.

Rotation of the carousel can be continuous or discontinuous. In continuous processing, the wafers are constantly rotating so that they are exposed to each of the injectors in turn. In discontinuous processing, the wafers can be moved to the injector region and stopped, and then to the region between the injectors and stopped. For example, the carousel can rotate so that the wafers move from an inter-injector region across the injector (or stop adjacent the injector) and on to the next inter-injector region where the carousel can pause again. Pausing between the injectors may provide time for additional processing between each layer deposition (e.g., exposure to plasma).

The frequency of the plasma may be tuned depending on the specific reactive species being used. Suitable frequencies include, but are not limited to, 400 kHz, 2 MHz, 13.56 MHz, 27 MHz, 40 MHz, 60 MHz and 100 MHz.

According to one or more embodiments, the substrate is subjected to processing prior to and/or after forming the layer. This processing can be performed in the same chamber or in one or more separate processing chambers. In some embodiments, the substrate is moved from the first chamber to a separate, second chamber for further processing. The substrate can be moved directly from the first chamber to the separate processing chamber, or the substrate can be moved from the first chamber to one or more transfer chambers, and then moved to the separate processing chamber. Accordingly, the processing apparatus may comprise multiple chambers in communication with a transfer station. An apparatus of this sort may be referred to as a "cluster tool" or "clustered system", and the like.

Generally, a cluster tool is a modular system comprising multiple chambers which perform various functions including substrate center-finding and orientation, degassing, annealing, deposition and/or etching. According to one or more embodiments, a cluster tool includes at least a first chamber and a central transfer chamber. The central transfer chamber may house a robot that can shuttle substrates between and among processing chambers and load lock chambers. The transfer chamber is typically maintained at a vacuum condition and provides an intermediate stage for shuttling substrates from one chamber to another and/or to a load lock chamber positioned at a front end of the cluster tool. Two well-known cluster tools which may be adapted for the present disclosure are the Centura® and the Endura®, both available from Applied Materials, Inc., of Santa Clara, Calif. However, the exact arrangement and combination of chambers may be altered for purposes of performing specific steps of a process as described herein. Other processing chambers which may be used include, but are not limited to, cyclical layer deposition (CLD), atomic layer deposition (ALD), chemical vapor deposition (CVD), physical vapor deposition (PVD), etch, pre-clean, chemical clean, thermal treatment such as RTP, plasma nitridation, degas, orientation, hydroxylation and other substrate processes. By carrying out processes in a chamber on a cluster tool, surface contamination of the substrate with atmospheric impurities can be avoided without oxidation prior to depositing a subsequent film.

According to one or more embodiments, the substrate is continuously under vacuum or "load lock" conditions, and is not exposed to ambient air when being moved from one chamber to the next. The transfer chambers are thus under vacuum and are "pumped down" under vacuum pressure. Inert gases may be present in the processing chambers or the transfer chambers. In some embodiments, an inert gas is used as a purge gas to remove some or all of the reactants after forming the layer on the surface of the substrate. According to one or more embodiments, a purge gas is injected at the exit of the deposition chamber to prevent reactants from moving from the deposition chamber to the transfer chamber and/or additional processing chamber. Thus, the flow of inert gas forms a curtain at the exit of the chamber.

During processing, the substrate can be heated or cooled. Such heating or cooling can be accomplished by any suitable means including, but not limited to, changing the temperature of the substrate support (e.g., susceptor) and flowing heated or cooled gases to the substrate surface. In some embodiments, the substrate support includes a heater/cooler which can be controlled to change the substrate temperature conductively. In one or more embodiments, the gases (either reactive gases or inert gases) being employed are heated or cooled to locally change the substrate temperature. In some embodiments, a heater/cooler is positioned within the chamber adjacent the substrate surface to convectively change the substrate temperature.

The substrate can also be stationary or rotated during processing. A rotating substrate can be rotated continuously or in discrete steps. For example, a substrate may be rotated throughout the entire process, or the substrate can be rotated by a small amount between exposures to different reactive or purge gases. Rotating the substrate during processing (either continuously or in steps) may help produce a more uniform deposition or etch by minimizing the effect of, for example, local variability in gas flow geometries.

While the foregoing is directed to embodiments of the present disclosure, other and further embodiments of the disclosure may be devised without departing from the basic scope thereof, and the scope thereof is determined by the claims that follow.

What is claimed is:

1. A plasma source assembly comprising:
   a wedge-shaped housing having a gas inlet and a front face defining a flow path, the gas inlet allowing a flow of gas to move along the flow path to pass through the housing and out the front face;
   an RF hot electrode within the housing, the RF hot electrode having a first surface oriented substantially parallel to the flow path and a serpentine shape; and
   a return electrode within the housing, the return electrode having a first surface oriented substantially parallel to the flow path and spaced from the first surface of the RF hot electrode to form a gap, the return electrode having a complementary shape to the RF hot electrode to maintain substantially the same gap along a length of the serpentine shape.

2. The plasma source assembly of claim 1, further comprising a second return electrode, the second return electrode having a first surface oriented substantially parallel to the flow path and spaced from a second surface of the RF hot electrode to form a second gap, the second surface of the RF hot electrode opposite the first surface of the RF hot electrode.

3. The plasma source assembly of claim 1, wherein the return electrode is a ground electrode.

4. The plasma source assembly of claim 1, wherein the return electrode is a powered electrode different from the RF hot electrode.

5. The plasma source assembly of claim 1, wherein the gap between the RF hot electrode and the return electrode is in the range of about 4 mm to about 15 mm.

6. The plasma source assembly of claim 1, wherein the gap between the RF hot electrode and the return electrode changes from a narrower gap adjacent the gas inlet to a wider gap adjacent the front face.

7. The plasma source assembly of claim 6, wherein the thickness of the RF hot electrode is greater adjacent the gas inlet than adjacent the front face.

8. The plasma source assembly of claim 1, wherein the RF hot electrode has a thickness in the range of about 3 mm to about 11 mm.

9. The plasma source assembly of claim 1, wherein the RF hot electrode has a height in the range of about 8 mm to about 40 mm.

10. The plasma source assembly of claim 1, wherein the RF hot electrode and return electrode extend along a major axis of the housing.

11. The plasma source assembly of claim 1, wherein the RF hot electrode and return electrode extend perpendicular to a major axis of the housing.

12. The plasma source assembly of claim 1, wherein the RF hot electrode has a plurality of fingers extending perpendicular to a major axis of the housing.

13. The plasma source assembly of claim 12, wherein the return electrode has a complementary shape to the RF hot electrode to maintain substantially the same gap between the RF hot electrode and the return electrode.

14. The plasma source assembly of claim 1, further comprising a spacer adjacent a lower edge of the RF hot electrode.

* * * * *